United States Patent
Matern et al.

[11] Patent Number: 5,976,121
[45] Date of Patent: Nov. 2, 1999

[54] MEDICAL MANIPULATOR

[75] Inventors: Ulrich Matern, Bollschweil; Peter Waller, Gauting, both of Germany

[73] Assignee: Karl Storz GmbH & Co., Germany

[21] Appl. No.: 08/793,741

[22] PCT Filed: Sep. 5, 1995

[86] PCT No.: PCT/DE95/01196

§ 371 Date: May 27, 1997

§ 102(e) Date: May 27, 1997

[87] PCT Pub. No.: WO96/07359

PCT Pub. Date: Mar. 14, 1996

[30] Foreign Application Priority Data

May 9, 1994 [DE] Germany .............................. 44 31 561

[51] Int. Cl.[6] .................................................. A61B 17/00
[52] U.S. Cl. .................................. 606/1; 606/45; 606/174
[58] Field of Search ........................... 606/1, 167, 174, 606/205–211, 19, 22, 32, 34, 37, 39, 40, 45–52

[56] References Cited

U.S. PATENT DOCUMENTS

| 5,295,956 | 3/1994 | Bales et al. ............................... 604/35 |
| 5,441,494 | 8/1995 | Oritz ........................................ 606/205 |
| 5,454,827 | 10/1995 | Aust et al. .............................. 606/205 |
| 5,669,875 | 9/1997 | Eerdenburg ............................. 606/205 |

Primary Examiner—Glenn K. Dawson
Attorney, Agent, or Firm—St. Onge Steward Johnston & Reens LLC

[57] ABSTRACT

A medical manipulating device (1), in particular, for endoscopic applications, having a medical instrument (3) disposed at the distal end, a grip (2) disposed at the proximal end, the grip (2) being provided with a grasping part (4) which can be held by hand, the grasping part (4) being provided with actuating elements which can be operated with the fingers, and a shank part (5), which connects the grip (2) to the instrument (3), and which is provided with transmission elements which transmit actuation of the actuating elements to the medical instrument (3).

24 Claims, 6 Drawing Sheets

MEDICAL MANIPULATOR

TECHNICAL FIELD

The present invention related to a medical manipulating device having a medical instrument disposed at the distal end, a grip disposed at the proximal end, and a shank part connecting the grip to the instrument, according to the generic part of claim 1.

Instruments of this type are utilized, by way of illustration, in endoscopy and, in particular, in minimal-invasive surgery.

STATE OF THE ART

A medical manipulating device according to the generic part of claim 1 is known from EP-A-0 546 767. A largely similar manipulating device is described in DE-A-41 36 861.

The known manipulating devices, which are particularly used in minimal-invasive surgery, have a grasping part in the form of a pistol handle. The grasping part is connected to a shank part at whose distal end a surgical instrument is disposed, by way of illustration, a gripper or a pair of scissors. The grip is provided on the side of the grasping part facing the surgical instrument with an actuating lever which is connected to the surgical instrument by means of a transmission connection.

Unfavorable is these known manipulating devices is, however, that when actuating the lever, the holding position of the hand has to be released so that the grip and the surgical instrument fixed thereto can no longer be grasped or guided firmly. In order to avoid faulty positioning of the, in many cases, very small surgical instrument, and the entailed risk of injury to the patient, the grip therefore has to be held with the other hand when adjusting or releasing the actuating lever on the grasping or the shank part connected thereto. Frequently, however, this other hand is needed in minimal-invasive surgery for carrying out other work, by way of illustration, operating measuring or monitoring devices.

The grip known from DE-A-41 36 861 is provided, on the side facing away from the surgical instrument, with two switches that can be actuated with the thumb for triggering electric devices. With these switches the surgical instrument at the distal end of the shaft can be rotated and swiveled. Unfavorable, however, is that both switches can be actuated only alternately with the thumb so that simultaneous rotating and swiveling of the surgical instrument is practically impossible. Moreover, in order to actuate the switch, the thumb has to be stretched out relatively far away from the hand so that the hand tires quickly during minimal-invasive surgery in which the surgeon has to frequently hold or actuate the surgical instrument by the grip for more than one hour.

DESCRIPTION OF THE INVENTION

The object of the present invention is to provide a medical manipulating device having a medical instrument disposed at the distal end, a grip at the proximal end, and a shank part connecting the grip to the instrument, with which the work of the medical manipulating device can be safely carried out for long periods of time without tiring. In particular, it should be possible to operate and position the instrument with only one hand. Moreover, with the manipulating device, holding and precise positioning should be possible without tiring.

An invented solution to this object is provided in claim 1. Further improvements of this manipulating device according to the present invention are the subject matter of claims 2 and the following claims.

According to the present invention, a generic manipulating device is further improved by a combination of the following features:

the grasping part is ergonomically shaped in such a manner that it can largely be grasped by one hand at least between the ball section and the metacarpus of the hand respectively the first row of phalanges of the hand and can be held without the use of at least the third and second joints of the index finger and the middle finger, at least for the index finger and the middle finger respectively a separate actuating element is provided of which each is designed in such a manner that when it is actuated with the free finger tip of the assigned finger, the rest of the hand and finger region remain essentially in a grasping respectively holding position.

The ergonomically shaped grasping part which can be grasped with the ball, the metacarpus and the first row of phalanges of the hand permits holding the grip for long periods of time in a relaxed way without tiring, with the hand being able to remain practically in its natural rest position while holding.

On the grasping part, finger supports are provided for the fingers at least in the region of the first row of phalanges of the index finger and the middle finger, on which the fingers partially lie in the holding position whereas the actuating elements are disposed in the region of the free finger tips. In this manner, these actuating elements can be easily operated without having to release the hand from the holding position. In this way, the grip permits in an advantageous manner firm holding of a medical instrument provided at the shank part. The individual actuating elements are assigned to the individual fingers in such a manner that several functions, by way of illustration a positioning movement of the medical instrument in multiple axes (for instance rotating and simultaneous tilting) and/or adjustment of the instrument in order to carry out a cutting or grasping motion can be carried out simultaneously.

In an advantageous further improvement it is provided that the actuating elements are designed for proportional transmission of the actuating movement. The actuating elements can, in particular, be designed in such a manner that their position indicates the position of the swiveling or rotating axis for the surgical or medical instrument assigned to this specific actuating element.

This design has the advantage that the operating person, by way of illustration a surgeon, can immediately conclude during minimal-invasive surgery from the position of the actuating element, by way of illustration, the position of the swiveling or rotating axis for the surgical or medical instrument assigned to this specific actuating element. In this way, manipulation can be conducted without immediate sight control.

Moreover, such an analog actuating element, which by way of illustration can be an analog tab, a rocker key or an analog swivel key, permits especially quick adjustment of the medical instrument. In triggering electric devices, such as by way of illustration motors or actuators and in particular micromechanical actuators disposed at the distal end, rotary potentiometers or the like can be used as analog elements.

It is further advantageous if keys, in particular swivel or rocker keys are provided as actuating elements at least for the index finger and the middle finger but also for the thumb, and if these keys can be pressed with the respective finger tip to counteract a restoring force. The joint of such a swivel key is preferably disposed adjacent to the finger joint located between the first row and second row of phalanges so that the swivel key when actuated practically executes the same swiveling movement as the free finger tip and therefore can be operated especially ergonomically. The swivel key can extend the entire length of the third row of phalanges in such a manner that the pressure force is distributed over a large as possible finger surface when actuating the swivel key.

In another invented improvement, at least one separate actuating element, in particular, a press key, a swivel key or a rotary element, is provided for the thumb. In this case, an additional function, by way of illustration adjusting the medical instrument about an additional axis such as the longitudinal axis of the shank part can be carried out with the thumb independently of and, if need be, parallel to the functions that can be actuated with the index finger and the middle finger without having to release the hand from the holding position to do so.

It is especially favorable if several actuating elements which can be selectively adjusted by the thumb are disposed in the grasping region of the thumb. Thus by way of illustration switches can be provided for switching a HF current on/off, for actuating suction removal and/or rinsing as well as locks for fixing other actuating elements so that all told there is a multiplicity of actuating elements which can all be adjusted with only some hand. The elements, which can be designed as a kind of so-called joy stick, can also be equipped with an additional switch, by way of illustration a press button switch, with which a function, by way of illustration a coagulator, a laser or the like is switched on or off.

A preferred improvement of the present invention provides that the shank part between the support respectively the actuating elements for the index finger and the middle finger is connected to the grasping part. In this case, in the holding position of the grip, the shank part lies as a straight extension of the extended hand-lower arm. A rotary movement of the lower arm about its longitudinal axis is thereby immediately transmitted to the shank part without the latter swerving laterally. In this way, the shank part inserted in a trocar tube can be turned inside the trocar tube to position the medical instrument in a simple manner.

Especially advantageous is furthermore if the grasping part is designed multipartite and if, in particular, multiple, exchangeable and different size ball parts are provided. By exchanging the ball part, the grip can be individually adapted to the respective user in a simple manner. In this way the grip permits users with different size or shaped hands to work for long periods of time without tiring.

Another advantageous embodiment of the present invention provides that at least one of the actuating elements is coupled to a fixing device for setting the actuating element in at least one end position and/or one or several intermediate positions. In this way the actuating element can be fixed so that it does not move accidently. Moreover specific function positions of the medical instrument, by way of illustration the grasping or open position of a gripper, can be set and fixed in a simple manner.

Especially advantageous is if a claiming means having a support area for the thumb is provided between the thumb and the carpus of the index finger. By firmly clamping the clamping means, the grip can then be held between the thumb and the carpus of the index finger, while the hand can temporarily release its grasping position.

Furthermore, it is useful if in the region of the finger supports, in particular for the little finger and the ring finger, molded grooves respectively raised separation means are provided between and/or beside the fingers. The grip can then be held better with the separation means and the molded grooves prevent the fingers from slipping off to the side.

In another invented embodiment, a thumb support, which preferably is a receiving impression or similar molded groove, is provided on the grip for the thumb. The thumb can then be supported in practically its natural rest position on the thumb support in such a manner that the grasping part, on the one hand, can be held in a non-tiring manner and, on the other hand, the holding forces can be transmitted better onto the grasping part.

Furthermore, especially favorable is if the medical instrument is borne in a rotatable manner about the longitudinal axis of the shank part, if a shaft is provided in the shank part which runs through the shank part in the longitudinal direction and is connected at its distal end region to the medical instrument in a turn resistant manner and if the shaft is connected to an actuating element, provided on the grasping part, by means of a driving connection. The medical instrument can in this way be easily turned in practically any direction in relation to the longitudinal axis of the shank part without turning the grip or turning the shank part, with the grip being able to remain in a position that is favorable for the surgeon. Depending on the application, it can be expedient if the actuating element for adjusting the direction of the medical instrument is an adjustment wheel, a swivel key or a press button key coupled to a step-by-step switch system that can, if need be, be switched in the direction of rotation.

An advantageous embodiment provides that the shaft is coupled directly or indirectly via a transmission to a rotary element or a similar actuating element which is preferably disposed in the thumb region on the grasping part. The medical instrument can in this way be turned about the shank part at any angle of rotation, with the transmission preferably being designed as a gear transmission, which translates the adjustment angle of the rotary element, while retaining the direction of rotation, into a larger adjustment angle of the surgical instrument in order to be able to position the latter simply and quickly.

Expediently, the shaft is designed as a hollow shaft in whose internal longitudinal cavity at least one transmission element for pull and/or pressure forces, in particular a pull/push rod or a Bowden pull cable, is provided. In addition to the rotary motion, other adjustment motions can then be transmitted to the medical instrument, which by way of illustration permit opening and closing a gripper and/or changing the angle of inclination of a medical instrument.

It is advantageous if at least one line, if need be formed by the internal longitudinal cavity of the hollow shaft, is provided in the shank part for entering and removing a fluid, in particular a rinsing fluid. Respective actuating elements can be provided on the grip for rinsing and/or suction extraction so that a surgery site to be treated can be easily cleaned immediately prior to the actual treatment.

A further improvement of the present invention provides that an actuating button, which can be swiveled laterally in at least two directions, is disposed on the grasping part, preferably in the thumb region, and that a transmission element which is coupled to the medical instrument acts on the actuating button. With such an actuating button, pull and pressure forces can be applied in the same manner with only one finger so that, by way of illustration, a swivel axis, which is coupled to the actuating button, for the medical instrument can be swiveled in both directions in a simple manner.

It is especially favorable if the actuating button can be swiveled in all four lateral directions and is provided with multiple, preferably four transmission elements which are 90 degrees off set respectively, preferably Bowden pull cables, acting on the actuating button. The actuating button can be coupled by means of the Bowden pull cables and a swivel device for the medical instrument, by way of illustration provided at the distal end of the shank part, with the respective swivel angle and the swivel direction of the actuating button being translated into a corresponding swivel angle respectively a corresponding swivel direction of the medical instrument. The actuating button permits in this manner simultaneous setting of the swivel angle and angle of inclination of the medical instrument in a simple manner with only one finger.

The improvement in which the grasping part can be disassembled for cleaning and/or is provided with holes respectively is composed of hole-structured elements, facilitates cleaning respectively sterilization which is especially critical for medical instruments.

BRIEF DESCRIPTION OF THE DRAWING

In the following the preferred embodiments of the present invention are made more apparent using the drawing. They show in different scale and partially very diagramatically.

DESCRIPTION OF PREFERRED EMBODIMENTS

In the following figures the same or corresponding parts bear the same reference numbers.

FIGS. 1 to 6 show a medical manipulating device generally designated 1. The manipulating device 1 has a grip 2 for a medical instrument 3, which is only depicted in FIGS. 5 and 6. The grip 2 has a grasping part 4, which can be grasped by the hand and on which actuating elements are disposed, which can be operated with the fingers and which will be described in more detail in the following.

Grasping part 4 is connected to shank part 5, which bears at the distal end the medical instrument 3. The actuating elements are connected to the medical instrument by means of a transmission connection, which can be realized, by way of illustration mechanically. However, in the case of distally disposed engines and/or actuators, which by way of illustration can be realized micromechanically, the transmission connection can, of course, also be realized electrically by means of control and energy supply lines.

The grasping part 4 is grasped by the hand and in particular between the ball of the hand and the metacarpus respectively the first row of phalanges. The shape of the grasping part 4 is adapted to the inside of the hand in a rest position in such a manner that the medical manipulating device 1 can be held in the hand for a long period practically without tiring.

Figure 3:
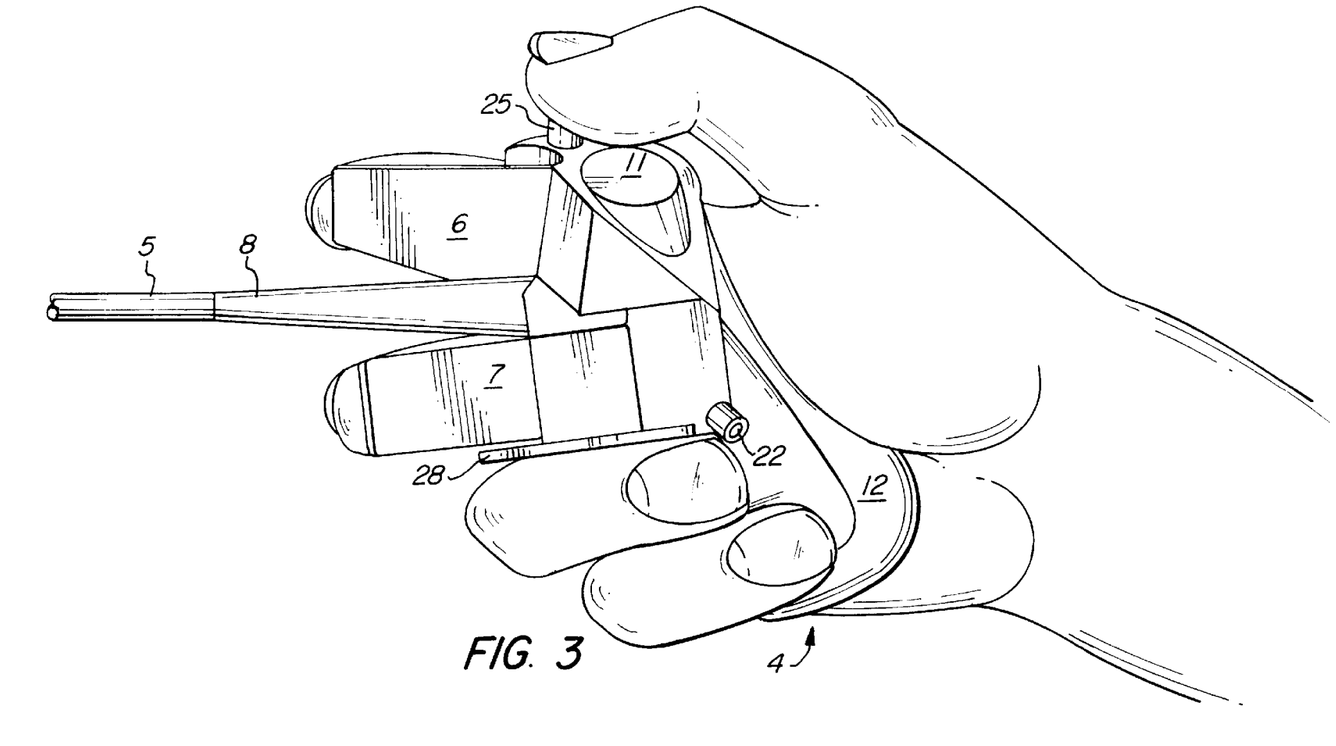
Figure 4:
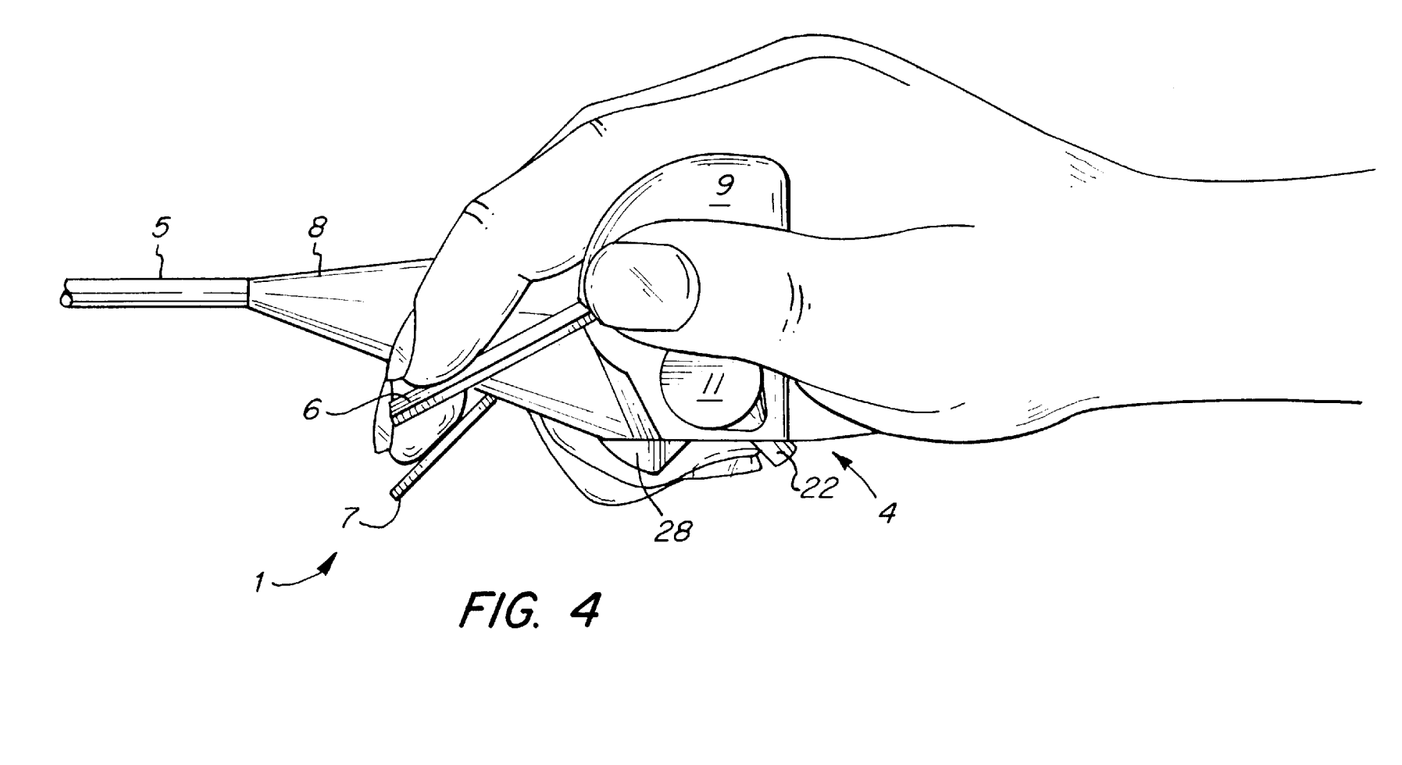

For the index finger and the middle finger, there are respective separate actuating elements, designed by way of illustration as swivel keys, 6, 7, which can be operated with the free finger tips of these fingers, whereas the rest of the hand and of the fingers can essentially remain in a grasping or holding position (FIGS. 3 and 4). The manipulating device 1 can, therefore, be firmly held with one hand even when actuating the swivel keys 6 and 7 thereby diminishing the risk of injury to the patent due to faulty positioning of the medical surgical instrument in minimal-invasive surgery, on the one hand, and on the other hand permitting the surgeon to operate the manipulating device with only one hand and leaving the other hand free for other work. It is also especially advantageous that the separate swivel keys 6,7, which are assigned to the index finger respectively the middle finger, can be operated independently and, if need be, simultaneously. However, instead of swivel keys other actuating elements, such as by way of illustration rocker keys or control elements for electric control devices, such as by way of illustration potentiometers, can of course be employed.

Figure 1:
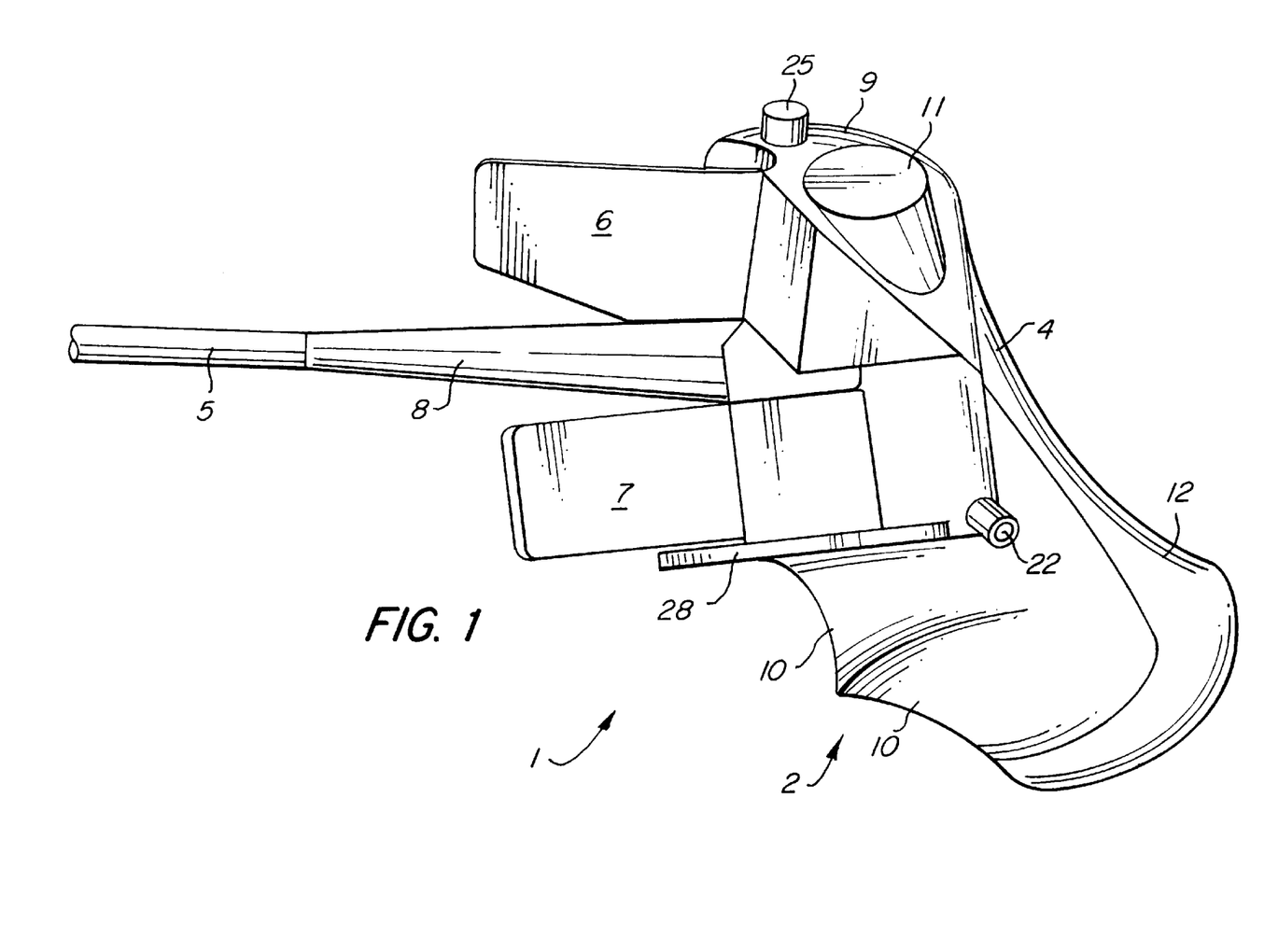
FIG. 1 a lateral view of the medical manipulating device, showing especially well the internal sides of the swivel keys with the index finger and the middle finger, the thumb support and the molded grooves for the ring finger and the little finger, FIG. 2 a top view of the manipulating device according to FIG. 1, showing especially well the laterally protruding clamping means on the top and the shank part widening in the transverse direction in the region of its proximal end, FIG. 3 a view of the inside of a hand with the manipulating device according to FIG. 1 in holding position, FIG. 4 an internal lateral view of a hand with the manipulating device according to FIG. 1 in holding position, FIG. 5 an exploded view of the manipulating device according to FIG. 1 with the disassembled ball part drawn with broken lines, with the mechanics contained in the grasping part drawn in and in which a rotary element is provided for rotating the medical instrument, and FIG. 6 a preferred embodiment of a manipulating device according to FIG. 1 in which an actuating button which can be swiveled in all side directions is provided for setting the angle of inclination and the direction of inclination of the medical instrument.
Figure 2:
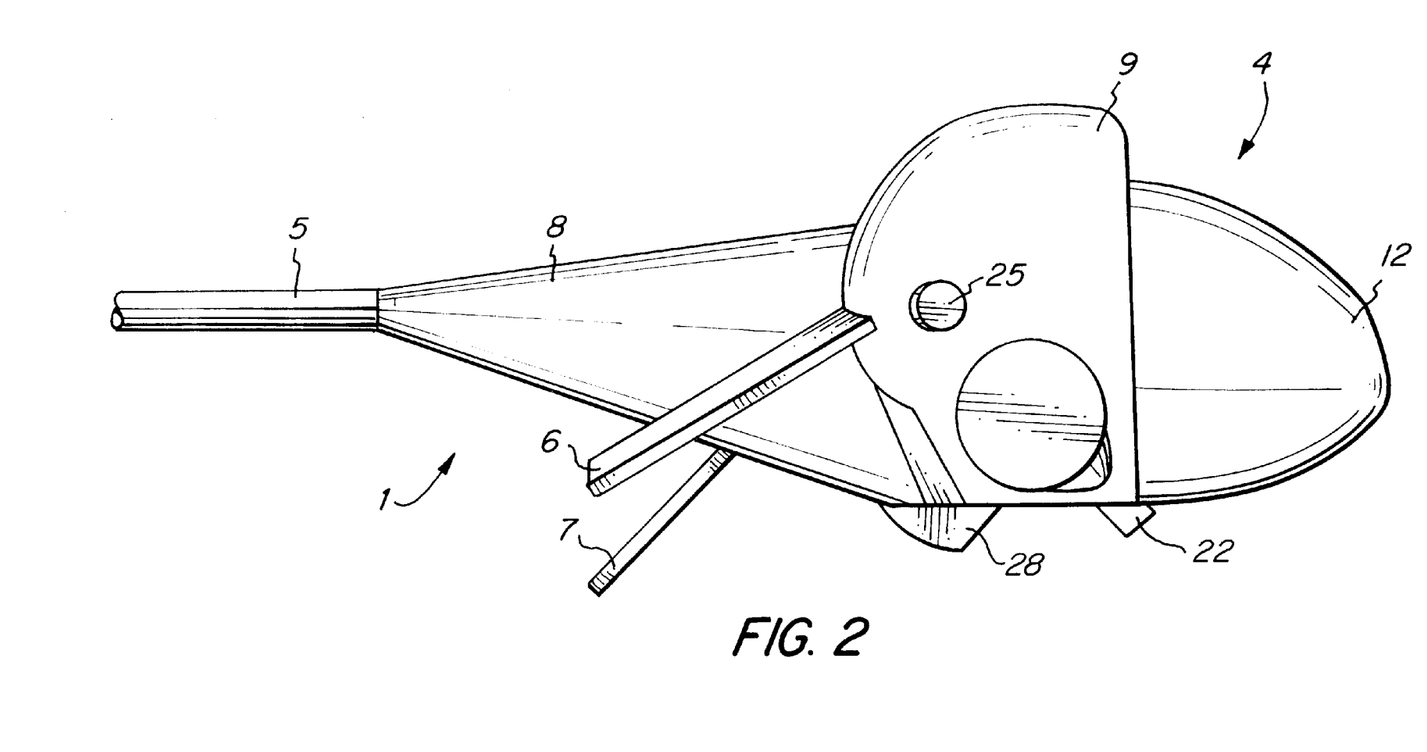

The view depicted in FIG. 1 shows very well that shank part 5 is connected between the swivel key 6 for the index finger and the swivel key 7 for the middle finger to the grasping part 4. There is an enlargement of the cross section of the shank part 5 in the region of its proximal end in the direction of the longitudinal axis of the swivel keys 6 and 7 respectively in the region of the index finger or middle finger in their holding position, this region being designed as a separation means 8. On the other hand, the separation means 8 grants the shank part 5 with flexural strength where it joins the grasping part 4 and, on the other hand, it provides a lateral guide for the index finger and the middle finger, preventing the fingers from interfering with the adjacent respective swivel key. Moreover, due to the separation means 8 in the transverse direction of the index finger and middle finger, the grasping part 4 in the holding position is positioned precisely in relation to the hand in such a manner that it always lies optimumly in the hand and practically cannot slip out of the hand even if the hand loosens the holding position slightly.

The shank 5 is disposed as a straight extension of the extended hand-underarm (cf. FIG. 4). If the shank part 5 is inserted into a trocar case, it can in this way be rotated in a simple manner about its axis of rotation if the hand-underarm is stretched out by rotating the hand respectively the underarm in the trocar case, obviating swiveling the arm laterally.

The support region between the thumb and carpus of the index finger, the grasping part 4 is provided with a clamping means 9 which extends outward and which can be clamped fast between the thumb and the carpus of the index finger when the hand is in the holding position. The grasping part 4 in this way can also be held by the thumb and the other fingers can be released from the holding position.

In order to prevent the fingers from slipping off the grasping part 4, molded grooves 10 running in a longitudinal direction of the fingers in the holding position and a separation means 28 on the grasping part for the little finger and the ring finger.

The grasping part 4 is provided with a thumb support 11 having a molded groove for fixing the thumb.

Figure 5:
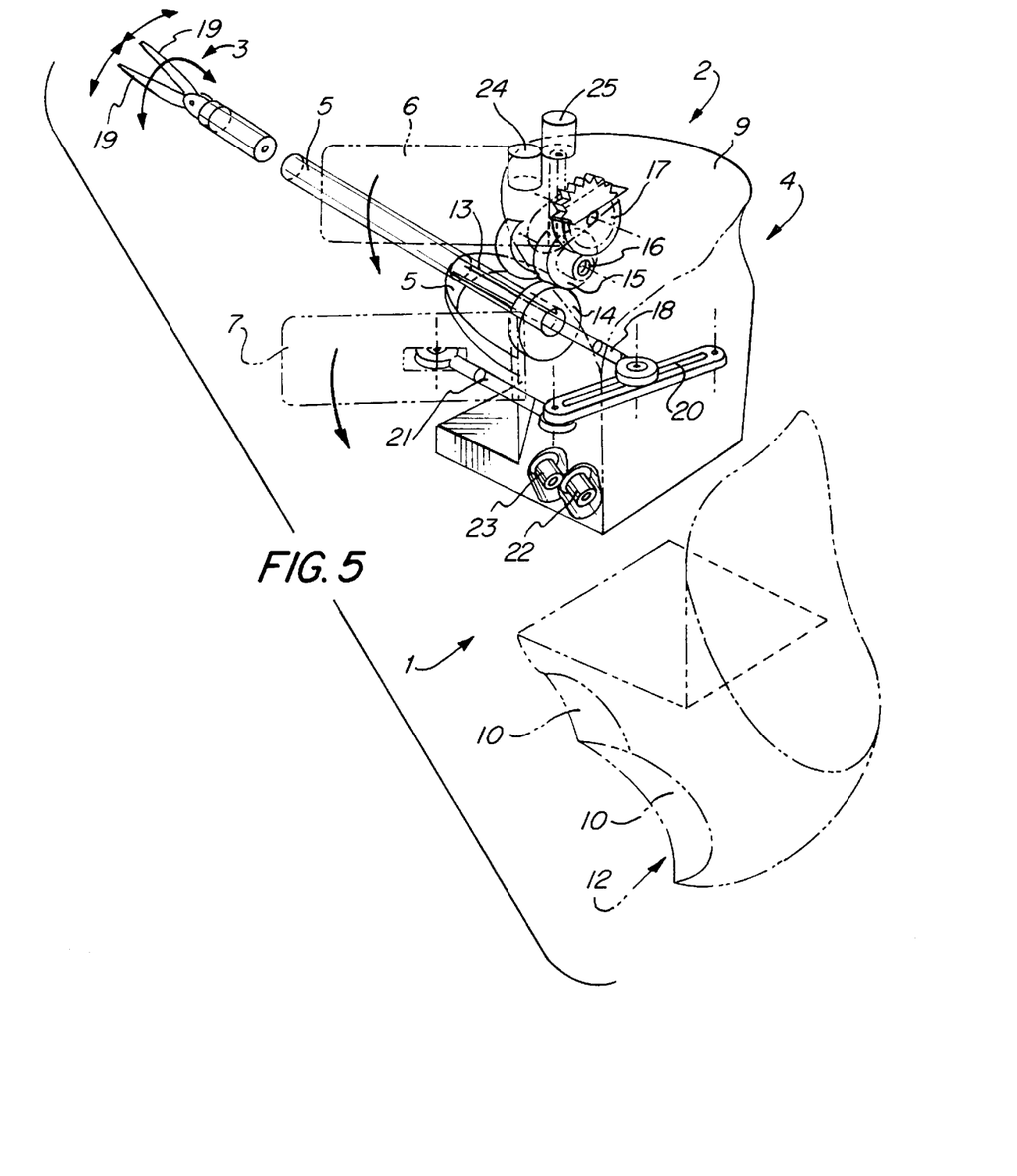
Figure 6:
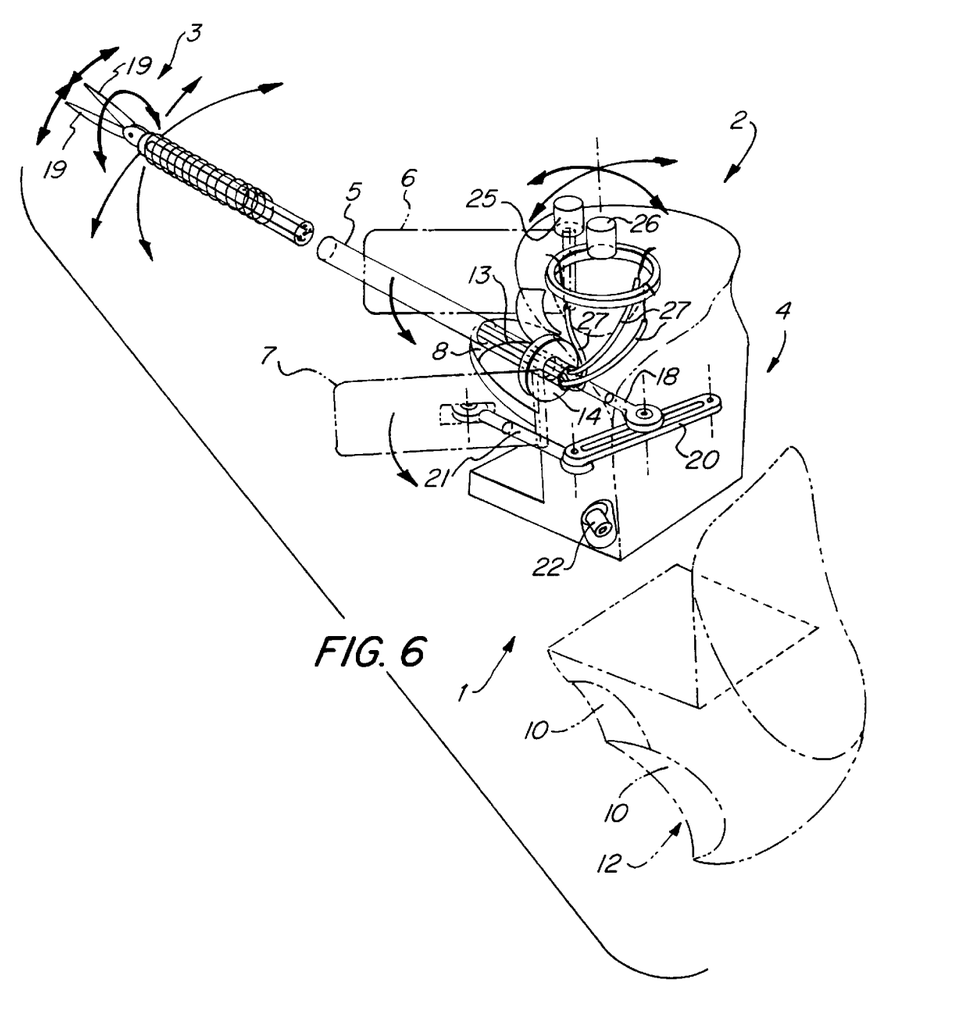

In order to be able to adapt the grasping part 4 even better to the different hands of the different users, it is designed multipartite and has an exchangeable ball part 12 (FIGS. 5 and 6). The manipulating device 1 can be provided with several, differently shaped or different size ball parts 12 which can be combined as desired. The grasping part 4 can in this way be formed in a simple manner according to the user's wishes.

In the preferred embodiment shown in FIG. 5, the medical instrument 3 is a pair of scissors. The scissors are connected to the front distal end of a hollow shaft 13 which runs through the shank part 5 in a longitudinal direction and is borne on the latter in such a manner that it can be rotated about the longitudinal axis of the shank part 5. An input gear 14 which engages with the teeth of a first intermediate gear 15 which has approximately the same diameter as the input gear 14, is provided at the proximal front end of the hollow shaft 13. The first intermediate gear 15 is joined single-piece with a smaller, second intermediate gear 16 which came with the external teeth of a rotary element 17 which is disposed in the thumb grasping part 4. The medical instrument 3 can in this way be rotated in a simple manner at any angle, thus more than 360 degrees, about the longitudinal axis of the shank part 5. The intermediate gears 15 and 16 translate the rotatry motion of the rotary element 17, while maintaining the direction of rotation, into a quicker rotary motion of the medical instrument 3.

A pull/push rod 18, which is coupled to the two parts 19 of the scissors of medical instrument 3, runs through the internal longitudinal cavity of the hollow shaft 13. The pull/push rod 18 can be moved axially in the hollow shaft 13. If the pull/push rod 18 is moved in the direction of the scissors parts 19 the free ends of the scissor parts 19 are moved away from each other and toward each other if the pull/push rod 18 is moved in the opposite direction. The pull/push rod 18 is connected in a flexible manner to a swivel lever 20, which is borne with one end section on the grasping part 4 in a swivelable manner and which is connected by means of a joint with its other end section to an actuating rod 21, which for its part is borne in a swivelable manner on the swivel key 7. The bearing is disposed approximately in the center on the bottom side of the swivel key 7. Furthermore, a restoring spring is provided on the swivel key 7 in such a manner that the scissors close by pressing the swivel key 7 with the free finger tip of the middle finger and return to their original position upon releasing the swivel key 7 due to the spring force of the restoring spring.

In the preferred embodiment shown in FIG. 5, moreover, a rinse connection 22 is provided on the grasping part 4 for rinsing which can be actuated with the swivel key 6 and a suction connection 23 which can be activated with the push button 24. The respective suction and rinsing conduits to the medical instrument 3 run through the hollow shaft 13.

Moreover, there is a push button 25 disposed on the upper side of grip 2 for applying a high frequency to the scissor parts 19. A monopolar high frequency device, having a respective counter electrode on the patient to be treated, or a bipolar high frequency device, having electrically mutually insulated scissor parts 19, can be employed.

As FIGS. 5 and 6 show especially well multiple actuating elements which are operated selectively with the thumb can be provided in the region of the thumb.

In the preferred embodiment according to FIG. 6, the distal end region of the shank part 5 can be designed elastically in the transverse direction, and four Bowden pull cables 27, with which the flexible section of the shank part 5 for setting the angle of inclination of the medical instrument 3 can be displaced laterally in any direction, are provided in the longitudinal internal cavity of the hollow shaft 13. Two Bowden pull cables 27 are assigned in pairs to a common function plane. The four Bowden pull cables 27 are coupled to an actuating button 26 which can be swiveled laterally in any direction with the thumb. These positions of the individual Bowden pull cables 27 engage the actuating button 26 90 degrees off set to each other in relation to the swivel axis of the actuating button 26 and at the same distances to the swivel axis of the actuating button. The Bowden pull cables 27 provided for a common function plane are disposed in pairs facing each other on the actuating button 26.

The actuating button 26 can be pressed down against the restoring force of an elastic spring element and is provided with a snap-in lock which stops the actuating button 26 from swiveling to the side if the latter is not manually actuated respectively pressed down. Thus the angle of inclination of the medical instrument 3 can be easily adjusted by pressing down the actuating button 26 with the thumb and is then laterally displaced. After releasing the actuating button 26, it locks automatically in such a manner that the medical instrument 3 remains in the previously set inclination. The thumb can then, if need be, return to its rest position. The actuating button 26 permits simultaneously setting the angle of inclination and the direction of inclination of the medical instrument 3. The hand can remain in the holding position. If need be, additional functions, such as by way of illustration executing cutting motions with the scissors and/or activating the rinsing or the suction can be conducted simultaneously with the swivel keys 6 and 7. Thus the medical instrument 3 can, as the diverse double arrows show in FIGS. 5 and 6, be versatilely adjusted using the manipulating device 1.

It must also be mentioned that the invented manipulating device is also suited for virtual surgery if it is combined with appropriate sensors.

Industrial Applicability

The aforedescribed medical manipulating device can be utilized in all fields of medicine and, in particular, in endoscopy. Especially advantageous is its application in minimal-invasive surgery.

What is claimed is:

1. A medical manipulating device (1) having
    a medical instrument (3) disposed at a distal end of the manipulating device,
    a grip (2) disposed at a proximal end of the manipulating device, said grip (2) being provided with a grasping part (4) which can be held by the hand, said grasping part (4) being provided with actuating elements which can be operated with fingers of the hand, and
    a shank part (5), which connects said grip (2) to said instrument (3), and which is provided with transmission elements which transmit actuation of said actuating elements to said medical instrument (3);
the improvement comprising:
    said grasping part (4) is ergonomically shaped to be grasped between a ball of the hand and a first row of the phalanges of the fingers and to be held without use of at least a third and second phalange of index and middle fingers of the hand, and wherein said grasping part (4)

is designed multipartite with exchangeable and different size parts being provided to match different hands, and a separate actuating element is provided for at least the index finger and the middle finger respectively, each said actuating element being designed in such a manner that upon being actuated with a free finger tip of the assigned finger, the rest of the hand and the fingers remain in a grasping position.

2. A manipulating device according to claim 1, characterized by said transmission elements being designed for proportional transmission of the actuation motion.

3. A manipulating device according to claim 2, characterized by said actuating elements being designed in such a manner that their position indicates the position of a swiveling axis assigned to at least one said actuating elements for said medical instrument.

4. A manipulating device according to claim 2, characterized by said actuating elements being selected from a group comprising analog tabs, rocker keys, analog electric control elements analog swivel keys, and combination of these.

5. A manipulating device according to claim 1, characterized by said actuating elements being pressable with the respective finger tip against a restoring force.

6. A manipulating device according to claim 1, characterized by at least one separate actuating element being provided for a thumb of the hand, said separate actuating element selected from a group comprising a press button key (24), a swivel key, a rocker key, and a rotary element (17).

7. A manipulating device according to claim 6, characterized by multiple actuating elements which can be selectively operated with the thumb.

8. A manipulating device according to claim 1, characterized by said shank part (5) being connected to said grasping part between the actuating elements for the index finger and the middle finger.

9. A manipulating device according to claim 8, characterized by said shank part (5) configured to be disposed approximately as a straight extension of an outstretched underarm of the hand.

10. A manipulating device according to claim 1, characterized by said actuating elements being selected from a group providing opening motions, closing motions, rotary motion and combinations of these to said medical instrument (3).

11. A manipulating device according to claim 1, characterized by said manipulating device (1) being provided with at least one fluid connection.

12. A manipulating device according to claim 1, characterized by at least one of said actuating elements being coupled to a lock-in device for locking the one of said actuating elements in at least one position.

13. A manipulating device according to claim 1, characterized by a clamping means (9) configured to be disposed on said grasping part in the region between a thumb and the first row of phalanges of a index finger of the hand.

14. A manipulating device according to claim 1, characterized by said grasping part being provided with molded grooves (10) and raised separation means (28).

15. A manipulating device according to claim 1, characterized by a support (11) being provided on the grasping part (4) for a thumb of the hand.

16. A manipulating device according to claim 1, characterized by said medical instrument (3) being borne on said shank part (5) in a rotatable manner about a longitudinal axis of said shank part (5), in said shank part (5) a shaft being provided which runs through said shank part (5) in a longitudinal direction and a distal end of said shaft being connected to said medical instrument (3) in a non-rotatable manner, and said shaft being connected to an actuating element provided at said grasping part (4) in a driving manner.

17. A manipulating device according to claim 16, characterized by said shaft being coupled via a transmission to a rotary element disposed on the grasping part (4).

18. A manipulating device according to claim 17, characterized by said shaft being guided in an axially shiftable manner in said shank part (5) to transmit an adjustment motion of said medical instrument (3).

19. A manipulating device according to claim 18, characterized by said shaft being designed as a hollow shaft (13), and in an internal longitudinal cavity thereof a transmission element being provided for longitudinal forces.

20. A manipulating device according to claim 1, characterized by in said shank part (5) at least one conduit being provided for fluid.

21. A manipulating device according to claim 1, characterized by said grasping part being disassemblable for cleaning.

22. A medical manipulating device (1) having
a medical instrument (3) disposed at a distal end of the manipulating device;
a grip (2) disposed at a proximal end of the manipulating device, said grip (2) being provided with a grasping part (4) which can be held by the hand, said grasping part (4) being provided with actuating elements which can be operated with fingers of the hand, and
a shank part (5), which connects said grip (2) to said instrument (3), and which is provided with transmission elements which transmit actuation of said actuating elements to said medical instrument (3);
the improvement comprising:
said grasping part (4) is ergonomically shaped to be grasped between a ball of the hand and a first row of the phalanges of the fingers and to be held without use of at least a third and second phalange of index and middle fingers of the hand;
a separate actuating element is provided for at least the index finger and the middle finger respectively, each said actuating element being designed in such a manner that upon being actuated with a free finger tip of the assigned finger, the rest of the hand and the fingers remain in a grasping position; and
an actuating button (26) which can be swiveled laterally in at least two directions being provided on said grasping part (4).

23. A manipulating device according to claim 22, characterized by said actuating button (26) being swivelable in all directions and multiple, transmission elements being provided which are 90 degrees offset to each other on said actuating button.

24. A medical manipulating device (1) having
a medical instrument (3) disposed at a distal end of the manipulating device,
a grip (2) disposed at a proximal end of the manipulating device, said grip (2) being provided with a grasping part (4) which can be held by the hand, said grasping part (4) being provided with actuating elements which can be operated with fingers of the hand, and
a shank part (5), which connects said grip (2) to said instrument (3), and which is provided with transmission elements which transmit actuation of said actuating elements to said medical instrument(3);

the improvement comprising:

said grasping part (4) is ergonomically shaped to be grasped between a ball of the hand and a first row of the phalanges of the fingers and to be held without use of at least a third and second phalange of index and middle fingers of the hand; and a separate actuating element is provided for at least the index finger and the middle finger respectively, each said actuating element being designed in such a manner that upon being actuated with a free finger tip of the assigned finger, the rest of the hand and the fingers remain in a grasping position;

said grasping part being provided with molded grooves (10) for receiving fingers therein and raised separation means (28) for separating adjacent fingers.

* * * * *